US00PP29128P2

(12) United States Plant Patent
Gerdts et al.

(10) Patent No.: US PP29,128 P2
(45) Date of Patent: Mar. 20, 2018

(54) PEACH TREE NAMED 'BURPEACHFORTYONE'

(50) Latin Name: *Prunus persica*
Varietal Denomination: Burpeachfortyone

(71) Applicants: Timothy J. Gerdts, Kingsburg, CA (US); John K. Slaughter, Fresno, CA (US)

(72) Inventors: Timothy J. Gerdts, Kingsburg, CA (US); John K. Slaughter, Fresno, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 15/530,586

(22) Filed: Feb. 2, 2017

(51) Int. Cl.
*A01H 5/08* (2006.01)

(52) U.S. Cl.
USPC ..... Plt./195

(58) Field of Classification Search
USPC ..... Plt./195
CPC ..... A01H 5/0856
See application file for complete search history.

*Primary Examiner* — Kent L Bell
(74) *Attorney, Agent, or Firm* — Randall Danskin P.S.

(57) ABSTRACT

A new and distinct variety of peach tree (*Prunus persica*), which is denominated varietally as 'Burpeachfortyone', and which produces an attractively colored white fleshed clingstone peach, with low malic acid which is further mature for harvesting and shipment approximately May 5 to May 10 under the ecological conditions prevailing in the San Joaquin Valley of central California.

1 Drawing Sheet

Botanical designation: *Prunus persica.*
Varietal denomination: 'Burpeachfortyone'.

BACKGROUND OF THE NEW VARIETY

The present variety of peach tree resulted from an ongoing program of fruit and nut tree breeding. The purpose of this program is to improve the commercial quality of deciduous fruit and nut varieties, and rootstocks, by creating and releasing promising selections of *Prunus, Malus, Punica* and *Juglans* species. To this end we make both controlled and hybrid cross pollinations each year in order to produce seedling populations from which improved progenies are evaluated and selected.

The seedling, 'Burpeachfortyone' was originated by us, and selected from a population of seedlings growing in our experimental orchards which are located near Fowler, Calif. The seedlings, grown on their own roots, were derived from an open-pollinated cross of an unpatented peach tree variety which was varietally denominated as 'N21.090', and which was the female parent. The pollen (male) parent of the new variety is unknown. The resulting fruit was collected from the female parent at a mature stage, and seeds were then extracted in May of 2008. After a period of stratification, the seed was established in an embryo rescue protocol which was performed by an outside third party, and who was employed by Inventors. The embryo rescue protocol which was employed by the outside third party utilized confidential and proprietary methodology owned by this same third party. This methodology is unknown to the Inventors. The embryo rescue protocol produce plantlets which later developed into small seedlings. After a development period the seedlings were placed in the greenhouse by population, and then field planted for tree establishment, and ultimately to exhibit fruit for evaluation. One white-fleshed peach seedling, which is the present variety, exhibited especially desirable characteristics, and was then designated as 'Q57.058' and subsequently re-named 'Burpeachfortyone'. This seedling was marked for subsequent observation. After the 2011 fruiting season, the new variety of peach tree was selected for advanced evaluation and repropagation.

ASEXUAL REPRODUCTION

Asexual reproduction of this new and distinct variety of peach tree was accomplished by budding the new peach tree onto 30 trees of 'Nemaguard' Rootstock (un-patented). This was performed by us in our experimental orchard which is located near Fowler, Calif. Subsequent evaluations of these asexually reproduced plants have shown those asexual reproductions run true to the original tree. All characteristics of the original tree, and its fruit, were established, and appear to be transmitted through these succeeding asexual propagations.

SUMMARY OF VARIETY

'Burpeachfortyone' is a new and distinct variety of peach tree, which is considered of relatively large size, and which has a vigorous growth characteristic. This new tree is also a regular and productive bearer of relatively large, firm, white-fleshed, low acidic clingstone fruit which have a very good flavor, and eating qualities. This new peach tree has a medium chilling requirement of approximately 350 hours, and further produces relatively uniformly sized fruit throughout the tree's canopy. In addition to the foregoing, the fruit of the new peach also appears to have good handling and shipping qualities. The 'Burpeachfortyone' peach tree bears fruit which are typically ripe for commercial harvesting and shipment on approximately May 5 to May 10 under the typical ecological conditions prevailing in the San Joaquin Valley of central California. In relative comparison to the 'Snow Angel' peach tree (U.S. Plant Pat. No. 18,750), which is the nearest commercial fruit tree comparator the current variety of fruit tree produces fruit which ripen approximately 4-6 days later. Further, the current variety of fruit tree produces fruit having soluble solid levels of about 15.5 degrees, (Brix), higher than the fruit produced by the 'Snow Angel' peach tree. In relative comparison to the parent tree, 'N21.090' (unpatented), the current peach tree variety produces fruit which have a white-flesh, while the parent tree produces fruit having a yellow flesh. Further, the current variety of peach tree ripens approximately 2 and a half weeks earlier than the 'N21.090' peach tree.

BRIEF DESCRIPTION OF THE DRAWINGS

The accompanying drawing, which is provided, is a color photograph of two whole mature fruit produced by a tree which is six years old, and which displays both the apical and basal aspects, thereof. One mature fruit is shown bisected, transversely, through the equatorial plane, and which reveals the flesh color, and stone characteristics thereof. The external coloration of the fruit as shown in the photograph is sufficiently matured for harvesting and shipment. The colors in this photograph are as nearly true as is reasonably possible in a color representation of this type. Due to chemical development, processing and printing, the leaves and fruit depicted in these photographs may, or may not be accurate when compared to the actual specimen. For this reason, future color references should be made to the color plates (Royal Horticultural Society, Fourth Edition, 2001) and descriptions provided, hereinafter.

NOT A COMMERCIAL WARRANTY:

The following detailed description has been prepared to solely comply with the provisions of 35 U.S.C. § 112, and does not constitute a commercial warranty, (either expressed or implied), that the present variety will, in the future, display all the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological details of this new and distinct variety of peach tree, the following has been observed during the sixth fruiting season, and under the ecological conditions prevailing at the orchards of the assignee which are located near the town of Fowler, county of Fresno, state of California. All major color code designations are by reference to The R.H.S. Colour Chart (Royal Horticultural Society, Fourth Edition, 2001) provided by The Royal Horticultural Society of Great Britain. Common color names are also occasionally used.

Tree:

*Size*.—Generally: Considered medium to medium-large in its growth pattern as compared to other common commercial peach cultivars ripening in the late season of maturity. The tree of the present variety was pruned to a height of approximately 270.0 cm. to about 310.0 cm. at commercial maturity.

*Width*.—Approximately 265.0 cm.

*Vigor*.—Considered moderately vigorous. The present peach tree variety grew from about 175.0 cm. to about 180.0 cm., in height, during the first growing season. The new variety was pruned to a height of approximately 150.0 cm. during the first dormant season, and primary scaffolds were then selected for the desired tree structure.

*Productivity*.—Productive. Fruit set varies from more than the desired crop load, to levels higher than desired amounts, when the new variety is grown in a suitable horticultural zone, and under appropriate commercial nursery conditions. The fruit set is spaced, by thinning, to develop the remaining fruit into the desired market-sized fruit. The number of the fruit set varies with the prevailing climatic conditions, and the cultural practices employed.

*Fruit bearing*.—Regular. Fruit set has been more than adequate during the previous years of observation, and thinning was necessary during the past 6 years on both the original seedling, and then on subsequent asexually reproduced trees.

*Tree form*.—Upright, and pruned into a vase shape.

*Density*.—Considered moderately dense. It has been discovered that pruning the branches from the center of the tree to obtain a resulting vase shape allows for enhanced air movement and appropriate amounts of sunlight to improve fruit color, and renewal of fruiting wood throughout the tree.

*Hardiness*.—The present tree was grown, and evaluated, in USDA Hardiness Zone 9. The calculated winter chilling requirements of the new tree is approximately 350 hours at a temperature below 7.0 degrees C. The present variety appears to be hardy under typical central San Joaquin Valley climatic conditions.

Trunk:

*Diameter*.—Approximately 17.5 cm in diameter when measured at a distance of approximately 15.24 cm. above the soil level. This measurement was taken at the end of the 7th growing season.

*Bark texture*.—Considered moderately rough, with folds of papery scarfskin being present. Since bark development, and coloration change with advancing tree age this characteristic varies with the tree vigor, age and regional conditions. Therefore, this is not a dependable descriptor of the new variety.

*Lenticels*.—Numerous flat, oval lenticels are present. The lenticels range in size from approximately 7.0 millimeters to about 11.0 mm. in width; and between about 1.0 and about 3.0 millimeters in height. The development and size of the trunk lenticels can be influenced, to some degree, by the ambient growing conditions, and are not, necessarily, a dependable characteristic of this variety. As trees of this variety mature, lenticels are present, but they are generally covered by increasing layers of cork (mature bark) and therefore become less apparent.

*Lenticel color*.—Considered an orange-brown, (RHS Greyed-Orange Group N172 D).

*Bark coloration*.—Variable, but it is generally considered to be a greyed-brown, (RHS Grey-Brown Group N199 B). This bark description was taken from trees in their sixth leaf, which have ruptured the scarf skin, and which further also have developed bark furrowing. This characteristic is much more typical of the bark of older trees. It should be noted that the coloration of the bark is influenced, and varies, as the smoother, darker background color approaches other bark features such as the lenticels, and the initial fissures which form a feature of the scarf skin development.

Branches:

*Size*.—Considered medium large for the variety.

*Diameter*.—Average, as compared to other common peach varieties. The branches have a diameter of about 10.0 centimeters when measured during the 6th year after grafting.

*Flowering shoot thickness*.—Approximately 5.0 to about 8.5 mm depending, at least in part, upon the type and form of the pruning regimen which is utilized, and the vigor of the flowering shoot which is selected during pruning.

*Surface texture*.—Average, and appearing relatively smooth, but with more furrowing on wood which is several years old.

*Crotch angles*.—Primary branches are considered variable, and are usually growing at an angle of about 44 to about 48 degrees when measured from a horizontal plane. This particular characteristic can vary due to the influence of variable ecological conditions, and cultural practices under which the tree is grown.

*Current season shoots*.—Surface texture — Substantially glabrous.

*Internode length*.—Approximately 2.3 cm.

*Color of mature branches*.—Approximately Grey-brown, (RHS Greyed-Orange Group 177 B).

*Current season's shoots*.—Color. — Light green, (RHS Green Group 138 B). The color of new shoot tips is considered a bright and shiny green, (RHS Green Group 134 A). The vegetative shoot color can be significantly influenced by plant nutrition, irrigation practices, and exposure to sunlight, and therefore this characteristic should not be considered a consistent botanical characteristic of this new variety.

Leaves:

*Size*.—Considered somewhat elongated, and narrow for the species. Leaf measurements have been taken from vigorous, upright, current-season growth, at approximately mid-shoot. It should be understood that the leaf size is often influenced by prevailing growing conditions, quality of sunlight, and the location of the leaf within the tree canopy. For this reason, leaf sizes can vary significantly based upon the ambient and other cultural factors listed above, and are not typically considered a dependable botanical descriptor.

*Leaf length*.—Approximately 148.0 to about 160.0 millimeters.

*Leaf width*.—Approximately 28.0 to about 30.0 millimeters.

*Leaf base-shape*.—The leaves generally exhibit uneven symmetry relative to the leaf longitudinal axis, with one margin slightly more acute nearing the petiole.

*Leaf form*.—Lanceolate.

*Leaf tip form*.—Acuminate.

*Leaf color*.—Upper Leaf Surface — A medium green, (approximately RHS Green Group 137 A).

*Leaf texture*.—Upper Leaf Surface — Glabrous. Lower Leaf Surface — Faintly glabrous, and having a more satin-like texture.

*Leaf color*.—Lower Leaf Surface — Medium green, (approximately RHS Green Group 137 D).

*Leaf venation*.—Pinnately veined.

*Mid-vein*.—Color — Considered a very pale green, (approximately RHS Yellow-Green Group 145 D).

*Leaf margins*.—Gently undulating. Form. — Considered finely crenate. Rarely, doubly crenate. Uniformity. — Considered generally uniform.

*Leaf petioles*.—Form. — Considered canaliculated, and having a more pronounced trough when viewed from the dorsal aspect. The petiole margin is considered rounded when viewed from the ventral aspect. Size. — Considered medium-small for the species. Length. — About 8.0 to about 11.0 mm. Diameter. — About 1.5 to about 2.0 mm. Color. — A light yellow-green, (approximately RHS Yellow-Green Group 145 B). Surface Texture. — Considered smooth, but with extremely fine pubescence. Strength. — Considered durable for the species until senescence.

*Leaf glands*.—Size. — Considered average for the species; approximately 2.5 mm. in length; and about 1.0 mm. in height. Number. — Generally one, and less common two glands appear per marginal side are found. Observations of more than two glands per marginal side are very uncommon. Type. — Glands located at the base of the leaf are predominantly reniform in shape. Color. — Considered a medium-dark brown, approximately (RHS Brown Group 199 A). Typically the coloration of the glands darkens, and occasionally begins to desiccate, with increasing senescence, during the mid-late growing season.

*Leaf stipules*.—Size. — Medium-large for this variety. Number. — Typically 2 per leaf bud, and up to 6 per shoot tip. Form. — Lanceolate in form, and having a serrated marginal edge. Color. — Green, (approximately RHS Green Group 139 B) when young, but graduating to a brown color, (approximately RHS Greyed-Orange Group 165 A) with advancing senescence. The leaf stipules are generally considered to be early deciduous.

Flower buds:

*Hardiness*.—No winter injury (bud death) has been noted during the last several years of observation in the central San Joaquin Valley. The new variety of peach tree has not been intentionally subjected to drought, cold or heat stress, and therefore this information is not available.

*Flower bud*.—Size — Variable, and dependent upon the state of maturity. The flower buds as described were observed approximately 7 days prior to bloom. Length — Approximately 14.5 millimeters. Diameter — Approximately 8.0 millimeters. Surface Texture. — Pubescent. Orientation. — Considered appressed, but appearing less so as the blossoms near opening.

*Bud scale color*.—Approximately RHS Greyed-Orange Group 175 A.

Flowers:

*Date of first bloom*.—Observed on Feb. 8, 2016. Blooming Time. — Considered average in relative comparison to other commercial peach cultivars grown in the central San Joaquin Valley. The date of full bloom was observed on Feb. 15, 2016. The date of full bloom varies slightly with climatic conditions, and prevailing cultural practices.

*Duration of bloom*.—Approximately 8 or more days. This particular characteristic varies slightly with the prevailing climatic conditions.

*Flower class*.—Considered a perfect flower, complete and perigynous.

*Flower type*.—The variety is considered to have a showy type flower.

*Flower size*.—Considered medium-large for the species. The flower diameter at full bloom, is approximately 48.0 to 54.0 millimeters.

*Bloom quantity*.—Considered very abundant.

*Flower bud density*.—Generally considered dense.

*Flower bud frequency*.—Generally two flower buds appear per node, occasionally one flower bud per node is observed. Very rarely three floral buds per node are observed.

*Petal size*.—Generally considered medium large for the species. Petal Length. — Approximately 22.0 to 25.0 millimeters. Petal Width. — Approximately 21.0 to 24.0 millimeters.

*Petal form*.—Considered broadly ovate.

*Petal count*.—Nearly always 5.

*Petal texture*.—Smooth, with extremely fine pubescence. Upper Petal Surface Texture. — Very finely pubescent, satin like. Lower Petal Surface Texture. — Very finely pubescent, satin like.

*Petal color*.—Considered a light pink at the popcorn stage, (RHS Red-Purple Group 65 C), and darkening with advanced senescence, and the exposure of sunlight, to a medium-dark pink, (RHS Red-Purple 63 D). This darkening of the petal is typically observed within the margins of the petal claw.

*Fragrance*.—Slight.

*Petal claw*.—Form. — The claw is considered ovate, and is generally large. Length. — Approximately 12.0 to 14.0 millimeters. Width. — Approximately 10.0 to 12.0 millimeters.

*Petal margins*.—Generally moderately undulate, and ruffled, especially apically.

*Petal apex*.—Often the petal apex does not exhibit a shallow recess at tip and is considered entire.

*Flower pedicel*.—Length. — Considered medium-long with an approximate length of about 1.5 to about 3.5 millimeters. Diameter. — Approximately 2.5 millimeters. Color. — Typically this is a medium brown, approximately (RHS Grey-Brown Group 199 B). However, this is dependent upon the age of the pedicel, the level of fruit maturity, and the timing of the visual observance. Strength. — Tenacious. This is considered average for the species. Surface Texture. — Generally smooth, to slightly undulate.

*Floral nectaries*.—Color. — Considered a very pale green (approximately RHS Yellow-Green Group 145 D).

*Calyx*.—Surface Texture. — Generally glabrous. Color. — A dull grey purple, (approximately RHS Greyed-Purple Group 185 B).

*Sepals*.—Upper Surface Texture. — Considered smooth, and weakly glabrous. Lower Surface Texture. — Pubescent. Number. — 5 sepals are present. Size. — Medium-large. Sepal Length. — Approximately 5.0 to 8.0 millimeters. Sepal Width. — Approximately 4.0 to 6.0 millimeters. Sepal Shape. — Generally obovate. Sepal Margin. — Considered smooth and entire. Sepal Color. — A dull grey-purple, (approximately RHS Greyed-Green Group 197 B).

*Anthers*.—Size. — Generally average in size. Color. — A dull red when viewed dorsally, and prior to dehiscence, (approximately RHS Greyed-Red Group 180 B). Position Relative to Stigma. — Generally the stigma is superior to the anthers by approx. 1.0-2.0 millimeters.

*Pollen production*.—Pollen is abundant, and has a yellow color, (approximately RHS Yellow-Orange Group 18 A).

*Fertility*.—Self-fertile.

*Filaments*.—Size. — Approximately 17.5 to 20.0 millimeters in length. Color. — Considered white (RHS Red Yellow Group 11 D).

*Pistil*.—Number. — Usually one, and only rarely more than one. Generally. — Large in size. Length. — Approximately 19.0 to about 22.0 millimeters in length including the ovary. Color. — Considered a very pale green, (approximately RHS Yellow-Green Group 149 D). Surface Texture. — The variety has a long pubescent pistil. Position Relative to Petals. — At flower maturity the stamens grow and extend to be superior to the petals.

Fruit:

*Maturity when described*.—Firm ripe condition (shipping ripe).

*Date of first picking*.—Approximately May 5, 2016.

*Date of last picking*.—May 10, 2016. The date of harvest can vary with the prevailing climatic conditions, crop loads, and the current cultural practices utilized to grow the tree.

*Size*.—Generally — Considered medium large.

*Average cheek diameter*.—Approximately 72.0 to about 75.0 millimeters.

*Average axial diameter*.—Approximately 70.0 to about 74.0 millimeters.

*Typical weight*.—Approximately 208.0 grams. This characteristics is quite dependent upon the prevailing cultural practices, and prevailing climatic conditions, and therefore is not a particularly distinctive characteristic of the new peach tree variety.

*Fruit form*.—Generally — Considered globose. The fruit is generally very uniform in symmetry.

*Mucron tip*.—Absent.

*Fruit suture*.—No stitching exists along the suture line.

*Suture*.—Color — Generally, the fruit appears blushed to the same degree as the skin, (approximately RHS Orange-Red Group 34 A).

*Ventral surface*.—Form — Considered even, and uniform in appearance, when it is viewed from the lateral, sutural plane.

*Apex*.—Shape — Rounded to slightly rutuse.

*Base*.—Shape — Generally smooth.

*Stem cavity*.—Shape/Size — The stem cavity is rounded-circular in form and is generally considered uniform. The stem cavity slightly extends toward the suture. The average depth of the stem cavity is about 8.0-10.0 mm. The average width of the stem cavity is about 26.0 mm. The average length of the stem cavity, when measured in the suturial plane. is about 45.0 mm.

*Fruit skin*.—Thickness. — Considered medium in thickness, and tenacious to the flesh. Surface Texture. — Short, fine and pubescent. The pubescence is moderately abundant. Taste. — Non-astringent. Tendency to crack. — Not observed in the previous years of observation, and evaluation.

*Fruit skin color*.—Blush Color. — Generally speaking, a red blush exists on a majority of the skin of the fruit (approximately RHS Orange-Red Group 34 A), and is more typically present on the portions of the fruit facing the sunlight. The blush of the fruit typically covers approximately 65%-85% of the fruit skin surface. The percentage of the blush on the fruit skin surface can vary, and is generally dependent upon the fruit's exposure to direct sunlight; specific fruit maturity; and also the prevailing ecological, and cultural conditions under which the fruit was grown.

*Ground color*.—A pale white-yellow, (approximately RHS. Yellow Group 11 D). The ground color of the fruit can vary significantly based upon the maturity of the fruit when this measurement is taken, and generally gains a lighter and less green cast with increasing maturity.

*Fruit glossiness*.—Fruit is not considered to be glossy.

*Fruit stem*.—Size. — Medium in length, approximately 6.0 to about 8.0 millimeters. Diameter. — Approximately 2.0 to about 3.0 millimeters. Color. — Pale yellow-green, (approximately RHS Yellow-Green Group N144 C).

*Fruit flesh*.—Ripening. — Considered even. Texture. — Firm, crunchy, juicy and dense. The flesh is considered firm-melting. Fibers. — Present, but not prominent. Aroma. — Slight. Eating Quality. — Considered very good. Flavor. — Considered balanced, with both sweetness, and low acidity. Juice Production. — Moderate. Brix. — About 12.0 to 14.5 degrees. This characteristic varies slightly with the number of fruit per tree; the maturity of fruit when harvested; the prevailing cultural practices which are employed; and the ambient climatic conditions under which the fruit was grown. Acidity. — Considered low. Approximately 0.3 titratable acidity. Acid levels assayed from fruit flesh can vary based upon the fruit maturity, sunlight exposure, ambient climatic conditions, and other regional and cultural practices which are utilized to grow the tree. Flesh Color. — It is considered white, (approximately RHS White Group 155 C). A slight pigmentation of a pink red color can be observed, and which radiates from the stone, (approximately RHS Red Group 39 A).

Stone:

*Type*.—Considered a clingstone.

*Size*.—It is generally considered to be medium to small for the species, the stone size varies significantly depending upon the tree vigor, the crop load, and the prevailing growing and cultural conditions under which the tree was grown.

*Length*.—Average, about 26.0 to about 30.0 millimeters.

*Width*.—Average, about 21.0 to about 23.0 millimeters.

*Diameter*.—Average, about 17.0 to about 20.0 millimeters.

*Form*.—Roughly ovoid.

*Stone base*.—Shape — The stone is considered shortly attenuate.

*Apex*.—Shape — The stone exhibits a slight acute apex.

*Stone surface*.—Surface Texture — Considered irregularly furrowed toward the apex. Further, more pitting exists in the mid-portion of the stone (laterally), and is more common toward the base. Ridges. — Ridging is generally more prominent, and is usually oriented parallel, and laterally relative at the ventral and dorsal margins. Ventral Edge. — The ventral edge is generally described as having adjoining ridges formed from each hemisphere. There are longitudinal grooves running alongside this joined ventral suture. Dorsal Edge. — Shape — Generally considered even. The folds of the surface ridges appearing on the external margins often end gently along the suture.

*Stone color*.—The color of a mature, dry stone is generally considered a dull brown, approximately (RHS Greyed-Orange Group 165 D). The stone color can vary considerably, based upon how recently the fruit has ripened, the degree of oxidation which has taken place, and any blanching which has occurred due to the exposure of the stone sunlight.

*Tendency to split*.—Splitting has rarely been noted.

*Kernel*.—Length. — Approximately 11.0-15.0 millimeters. Width. — Approximately 10.0-13.0 millimeters. Thickness. — About 4.0-6.0 millimeters. Size. — The kernel is considered medium in size for this early season ripening peach tree variety. Form. — Considered generally ovoid. The fruit of the current variety typically ripens before the kernel has had time to develop completely, and is considered gelatinous, and principally exhibits translucent cotyledons. The consistency and form of the kernel can vary, and often can shrivel, particularly at the base. Kernel Surface Texture. — The kernel pellicle is shortly pubescent. Color. — A pale tan (RHS Yellow-White Group 158 B).

*Use*.—The present variety 'Burpeachfortyone' is considered to be a peach tree of the late season of maturity, and which produces fruit which are considered to be firm, attractively colored, and which are useful for both local and long distance shipping.

*Keeping quality*.—Appears excellent. The fruit of the present variety has stored well for periods of up to 35 days after harvest at 1.0 degree Celsius.

*Shipping quality*.—Good. The fruit of the new peach tree variety showed minimal bruising of the flesh or skin damage after being subjected to normal harvesting and packing procedures.

*Resistance to insects and disease*.—No particular susceptibilities were noted. The present variety has not been intentionally tested to expose or detect any susceptibilities or resistances to any known plant, fruit diseases, insect, frost, winter injury or other ambient environmental factors.

Although the new variety of peach tree possesses the described characteristics when grown under the ecological conditions prevailing near Fowler, Calif., in the Central part of the San Joaquin Valley of California, it should be understood that variations of the usual magnitude, and characteristics incident to changes in growing conditions, fertilization, nutrition, pruning, pest control, frost, climatic variables and changes in horticultural management are to be expected.

Having thus described and illustrated our new variety of peach tree, what we claim is new, and desire to secure by plant Letters Patent is:

1. A new distinct variety of peach tree, substantially as illustrated and described, and which is characterized principally as to novelty by producing an attractively colored white fleshed clingstone peach with low malic acid, and which is further mature for harvesting and shipment approximately May 5 to May 10, under the typical ambient ecological conditions prevailing in the San Joaquin Valley of central California.

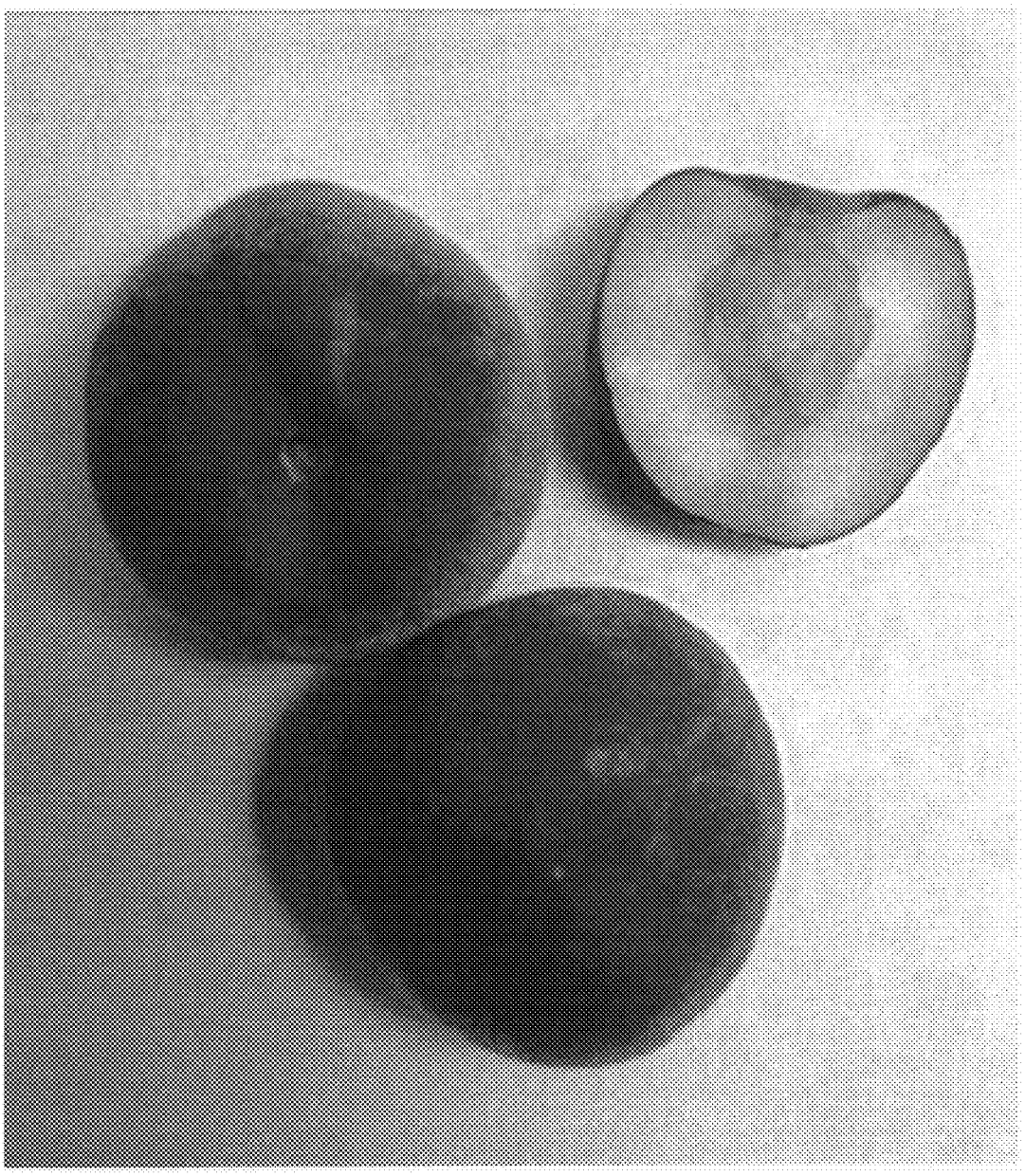

* * * * *